United States Patent [19]

Handelman

[11] 4,301,916
[45] Nov. 24, 1981

[54] CARRYING CASE FOR CONTRACEPTIVE DEVICES

[76] Inventor: Susan Handelman, 2910 Orchard La., Wilmette, Ill. 60091

[21] Appl. No.: 138,213

[22] Filed: Apr. 7, 1980

[51] Int. Cl.³ .............................................. F42B 39/02
[52] U.S. Cl. ......................................... 206/38; 150/7; 206/256; 206/260
[58] Field of Search .................... 206/38, 37, 570, 571, 206/581, 229, 256, 257, 258, 260, 268, 273, 370; 150/7

[56] References Cited

U.S. PATENT DOCUMENTS

| | | | |
|---|---|---|---|
| 1,183,800 | 5/1916 | Dalitz | 150/7 X |
| 1,521,897 | 1/1925 | Martin | 150/7 |
| 1,530,214 | 3/1925 | Stanley | 206/256 |
| 1,688,699 | 10/1928 | Gardner, Jr. | 206/256 |
| 3,552,610 | 1/1971 | Coleman et al. | 206/38 R |
| 3,949,916 | 4/1976 | Yount | 206/260 X |

Primary Examiner—Steven M. Pollard
Attorney, Agent, or Firm—Laff, Whitesel, Conte & Saret

[57] ABSTRACT

A compact carrying case for contraceptive devices has a series of pouches and a compartment which hold various elements used in a birth control system. The pouches have an entrance side which has elastic closing means for holding partially enclosed devices in place. A lid is hingedly attached to the bottom of the case adjacent the open ends of the pouches. The compartment fully encloses an additional device in one of two ways, both of which permit easy cleaning. A compartment having an entrance edge may be provided with a flap which covers the edge and fastens shut. The edge itself may expand, or expanding sides may be provided on the compartment, for easy cleaning. In the alternative, the compartment may be hingedly attached to the bottom and have an elastic opening in the side adjacent the pouches. The case may be closed by folding the compartment over the pouches and fastening the lid of the case to the outside of the compartment. The compartment may be opened and unfolded for easy cleaning.

3 Claims, 4 Drawing Figures

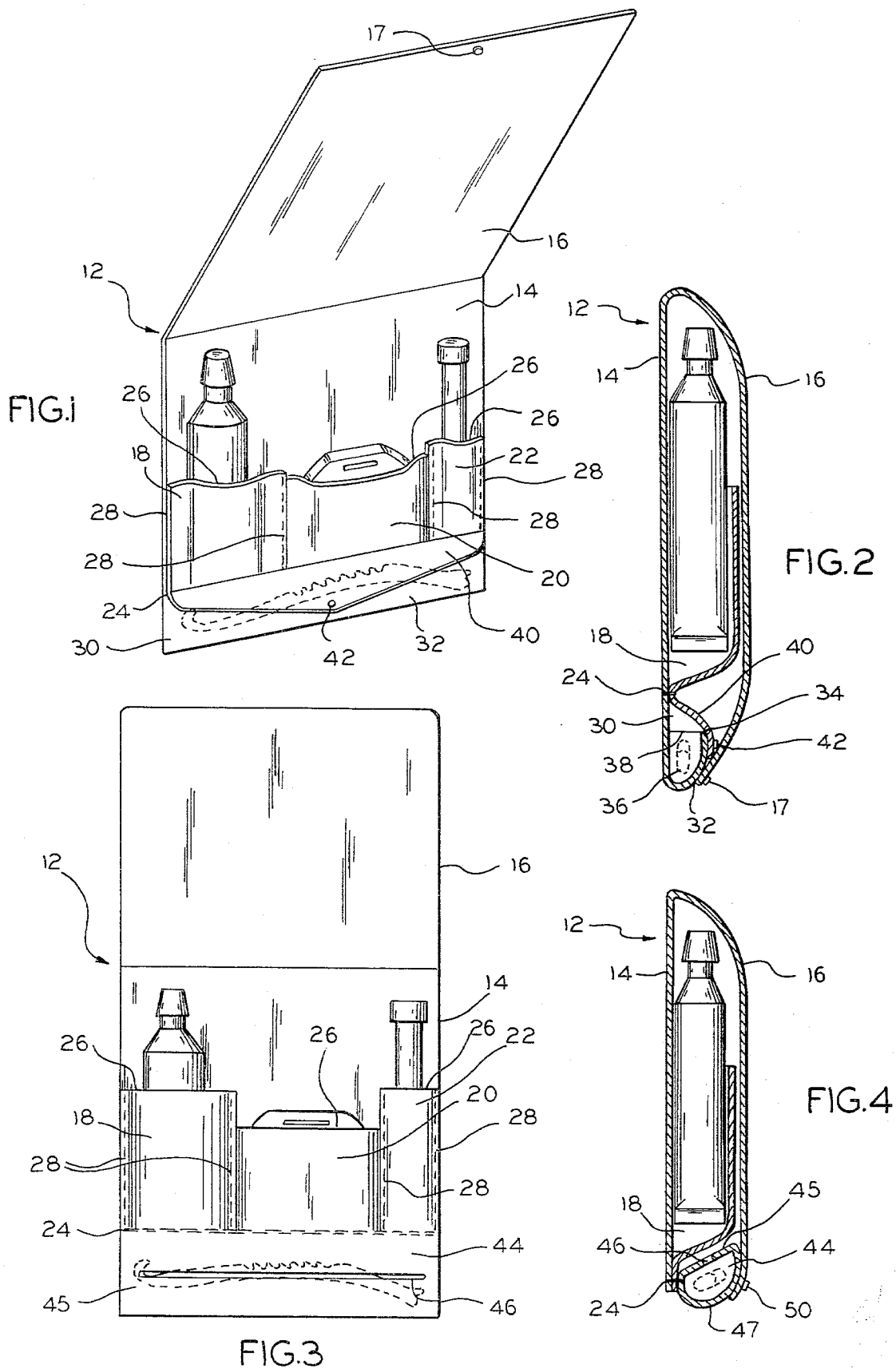

4,301,916

CARRYING CASE FOR CONTRACEPTIVE DEVICES

This invention relates to carrying cases for contraceptive devices, and more particularly to compact carrying cases which may be cleaned easily.

BACKGROUND OF THE INVENTION

Various methods of contraception have been developed to prevent pregnancy. Some are relatively unreliable, while others may cause harmful side effects and present potential health hazards to the user. The use of a diaphragm as a method of contraception has become increasingly popular because it is relatively reliable and safe.

A contraceptive diaphragm is generally stored in a hard, plastic cover. Use of the diaphragm usually requires several ancillary articles, including a chemical jelly, which is generally purchased in a tube, an introducer for inserting the diaphragm into the body, and an applicator for putting additional jelly on the diaphragm without removing it from the body. Each of these devices is generally purchased in individual packages, and is often carried loosely and unorganized in a handbag or purse.

Thus, there is a need for carrying cases for contraceptive devices, and particularly for a diaphragm and related accessories, which organize them in a sanitary enivronment and fit inside many handbags or the like.

Accordingly, an object of this invention is to provide new and inventive carrying cases for contraceptive devices, and particularly for diaphragms and related apparatus. Another object is to provide new and improved carrying cases for contraceptive devices, which cases hold and organize the devices under relatively sanitary conditions. Yet another object is to provide new and improved carrying cases for contraceptive devices, which cases are easy to clean, especially in the area where the introducer is stored. Still another object is to provide new and improved carrying cases for contraceptive devices which are relatively compact and flexible.

In keeping with one aspect of the invention, a carrying case for contraceptive devices includes a series of pouches which hold various objects, such as a tube of chemical jelly, a diaphragm cover, and an applicator. The case is somewhat flexible, and is compact enough to fit inside of many handbags or the like. The pouches have elastic closing means on their entrance sides to hold objects of different sizes, including partially used jelly tubes. A compartment for a diaphragm introducer may be provided in the form of a pocket and a flap which covers the entrance edge of the compartment and snaps shut over it. The case may be closed by fastening a lid over the pouches and compartment. The lid helps hold the objects in the pouches in place. In an alternate embodiment, the introducer compartment may be hingedly attached to the carrying case. The compartment is a pouch which is closed elastically in the center. The case may be closed by folding the compartment toward the pouches and snapping the lid of the case to the back of the compartment.

DESCRIPTION OF THE DRAWINGS

The above-mentioned and other features of the invention and the method of obtaining them will become more apparent and the invention itself will be best understood by reference to the following description of the invention taken in conjunction with the accompanying drawings, in which:

FIG. 1 is a perspective view of the inventive carrying case with a flap which covers the introducer compartment;

FIG. 2 is a cross-sectional elevation view of the inside of the carrying case of FIG. 1;

FIG. 3 is a front plan view of the inside of the inventive carrying case with a folding introducer compartment; and FIG. 4 is a side elevation view of the carrying case of FIG. 3.

DETAILED DESCRIPTION OF THE INVENTION

The carrying case 12 (FIGS. 1 and 2) includes a bottom 14 and a lid 16 which covers the bottom 14. The lid 16 is hingedly mounted on one side of bottom 14, and may be secured to the case 12 by any suitable lid fastening means 17.

A series of pouches 18, 20 and 22 are attached to the bottom 14. Pouches 18, 20 and 22 have a common bottom edge 24 and an entrance side 26. The closed sides 28 of the pouches 18, 20 and 22 are secured to the bottom 14. The common bottom edge 24 (FIGS. 1 and 2) may be secured to the bottom 14 some distance above the lower edge of the bottom 14.

The entrance side 26 of the pouches 18, 20 and 22 may include an elastic band or the like to hold different sized objects in the pouches, such as different sized diaphragm cases, or different sized jelly tubes. Also, the size of the jelly tube decreases as the jelly is used. The elastic closing means allows the pouches to hold these various sized objects securely.

The jelly, diaphragm cover and applicator are generally not fully enclosed in the pouches 18, 20 and 22. The exposed portions of the devices are covered and held in the pouches by the lid 16.

A compartment 30, which encloses the introducer, has a lower edge 32 and an entrance edge 34, and is attached to the bottom 14 beneath the common edge 24 (FIG. 1). The compartment has enough material so that the inside of the compartment may be fully exposed, for cleaning.

Sides 36 may also be provided on each side of the compartment 30 (FIG. 2), if desired, with a flexible, folding or elastic top 38. the sides 36 facillitate opening of the compartment 30 for cleaning.

A flap 40, which covers the entrance edge 34 of compartment 30, is attached to the bottom 14 above the entrance edge 34 at or near common edge 24. Any suitable flap fastening means 42 (such as a snap fastener) keeps the flap 40 closed. The lid 16 may be fastened to the outside of compartment 30 or to the bottom 16 by any suitable lid fastening means 17.

The embodiment of FIGS. 3 and 4 is the same as that of FIGS. 1 and 2, except as will now be described. The introducer compartment 44 is a relatively flexible pouch having an elasticized opening 46 in one side (FIG. 4). Compartment 44 is hingedly attached to the bottom 14, and includes a front side 45 adjacent the pouches, and a back side 47 opposite front side 45. When it is folded down, as in FIG. 3, the opening 46 is exposed so that the introducer may be inserted or removed or the compartment 44 cleaned, if desired.

Compartment 44 may be folded towards the pouches 18, 20 and 22, as shown in FIG. 4. Lid fastening means 50 are provided to secure the back side 47 of the compartment 44 to the lid 16, to close the case 12.

The manner in which the elements function may now be explained. The diaphragm is placed in a plastic diaphragm cover. The jelly, diaphragm cover and applicator are stored in pouches 18, 20 and 22 when lid 16 is moved away from entrance sides 26. Elastic bands along the entrance sides 26 hold the devices in place. The pouches 18, 20 and 22 may, however, be emptied and opened enough to allow the inside of each pouch to be cleaned.

The compartment 30 shown in FIGS. 1 and 2 is preferably used to hold the diaphragm introducer. The compatment 30 also may be expanded for easy cleaning, whether the entrance edge 34 is attached to the bottom 14 or compartment sides 36. Cleanliness in the compartment is especially important if it is used to store the introducer, because the introducer comes into intimate contact with the body each time the diaphragm is used. The flap 40 covers the entrance edge 34 of compartment 30, to maintain the introducer in a clean environment.

When all of the devices are in place in the bottom 14, the case 12 may be closed by covering the devices with lid 16 and fastening the lid to the outside of compartment 30 or bottom 14 by suitable fastening means 17. When the case 12 is closed, the devices are stored in an organized manner, and do not come into contract with other, perhaps unsanitary objects.

The compartment 44 shown in the embodiment of FIGS. 3 and 4 may be emptied and cleaned by first disconnecting lid fastening means 50 from the back side 47 of compartment 44, lifting lid 16 and unfolding compartment 44. The compartment 44 may be opened and cleaned by expanding the elastic opening 46. When the case 12 is closed, the devices are stored in an organized manner and are generally isolated from foreign objects which may be unsanitary.

The many advantages of this carrying case are now apparent. Contraceptive devices, particularly diaphragms with related accessories, may be stored in a sanitary, organized manner which protects them from contact with unsanitary objects. Also, the case itself may be easily cleaned, to maintain the devices in a relatively sanitary environment.

While the principles of the invention have been described above in connection with specific apparatus and applications, it is to be understood that this description is made only by way of example and not as a limitation on the scope of the invention.

I claim:

1. A compact carrying case for contraceptive devices comprising
    a bottom;
    more than one pouch attached to said bottom, each of said pouches having an entrance side and a common bottom edge;
    means to elastically close said entrance side of each of said pouches;
    a compartment attached to said bottom adjacent said common bottom edge, said compartment having an entrance edge;
    a flap attached to said bottom near said common bottom edge and adjacent said entrance edge;
    means for fastening said flap to said compartment to cover said entrance edge;
    a lid hingedly attached to said bottom near the entrance sides of said pouches; and
    means for fastening said lid to the outside of said compartment to cover said pouches and said compartment.

2. The compact carrying case of claim 1 wherein said compartment further includes expandable sides.

3. A compact carrying case for contraceptive devices comprising
    a bottom;
    more than one pouch attached to said bottom, each of said pouches having an entrance side and a common bottom edge;
    elastic closing means on each of said entrance sides of said pouches;
    a compartment hingedly attached to said bottom adjacent said common bottom edge;
    said compartment having a front side adjacent said pouches, a back side opposite said front side, and an elastic opening in said front side of said compartment;
    a lid hingedly attached to said bottom near said entrance sides of said pouches; and
    lid fastening means for securing said lid to said back side of said compartment.

* * * * *